US006271213B1

United States Patent
Henderson et al.

(10) Patent No.: US 6,271,213 B1
(45) Date of Patent: *Aug. 7, 2001

(54) AMINOSUGAR, GLYCOSAMINOGLYCAN, AND S-ADENOSYLMETHIONINE COMPOSITION FOR THE TREATMENT AND REPAIR OF CONNECTIVE TISSUE

(75) Inventors: Robert W. Henderson, Baldwin; Tarek Hammad, Baltimore, both of MD (US)

(73) Assignee: Nutramax Laboratories, Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/797,294

(22) Filed: Feb. 7, 1997

Related U.S. Application Data (63) Continuation-in-part of application No. 08/779,996, filed on Dec. 23, 1996.

(51) Int. Cl.$^7$ .................. A61K 31/715; A61K 31/70
(52) U.S. Cl. .................. 514/53; 514/54; 514/62; 514/46
(58) Field of Search .................. 514/54, 53, 62, 514/46

(56) References Cited

U.S. PATENT DOCUMENTS

| | | | |
|---|---|---|---|
| 3,232,836 | 2/1966 | Carlozzi et al. | 167/65 |
| 3,371,012 | 2/1968 | Furuhashi | 167/59 |
| 3,683,076 | 8/1972 | Rovati | 424/180 |
| 3,697,652 | 10/1972 | Rovati et al. | 424/180 |
| 4,006,224 | 2/1977 | Prudden | 424/180 |
| 4,465,672 | 8/1984 | Gennari | 424/180 |
| 4,473,551 | 9/1984 | Schinitsky | 424/95 |
| 4,486,416 | 12/1984 | Soll et al. | 424/180 |
| 4,543,408 | 9/1985 | Gennari | 536/26 |
| 4,647,453 | 3/1987 | Meisner | 424/54 |

(List continued on next page.)

FOREIGN PATENT DOCUMENTS

| | | | |
|---|---|---|---|
| 2609397 | 7/1988 | (FR) | A61K/31/70 |
| WO 92/15614 | 9/1992 | (WO) . | |

OTHER PUBLICATIONS

Vidal y Plana et al, "Articular Cartilage Pharmacology: I. In Vitro Studies on Glucosamine and Non–Steroidal Anti–inflammatory Drugs," Pharmacological Research Communication, 10 (6) 557–569 (1978).

Murray, "A Natural Treatment of Osteoarthritis," MPI's Dyanmic Chiropratic, pp. 8–10, Sep. 12, 1993.

Morrison et al, "Coronary Heart Disease and the Mucopolysaccharides (Glycosaminoglycans)," C.C. Thomas, Publisher, 1973, pp. 12–13; 109–127.

(List continued on next page.)

Primary Examiner—Gary Geist
Assistant Examiner—Everett White
(74) Attorney, Agent, or Firm—Covington & Burling (57) ABSTRACT

A composition for the protection, treatment and repair and for reducing the inflammation of connective tissue in mammals and a method for the treatment of connective tissue in mammals by the administration of the composition. The composition includes S-Adenosylmethionine (SAM), and a component selected from an aminosugar or salts thereof (e.g., glucosamine) or glycosaminoglycans (e.g., chondroitin salts) or mixtures or fragments thereof. The composition optionally includes manganese which promotes the production of connective tissue matrix. The composition also optionally includes methyl donors or methyl donor cofactors, such as vitamin B12, vitamin B6, folic acid, dimethylglycine or trimethylglycine.

13 Claims, 3 Drawing Sheets

U.S. PATENT DOCUMENTS

| | | | |
|---|---|---|---|
| 4,772,591 | 9/1988 | Meisner | 514/62 |
| 4,801,619 | 1/1989 | Lindblad | 514/825 |
| 4,870,061 | 9/1989 | Speck | 514/62 |
| 4,983,580 | 1/1991 | Gibson | 514/2 |
| 4,990,606 | 2/1991 | Gennari | 536/26 |
| 5,102,791 | 4/1992 | Gennari | 435/113 |
| 5,128,249 | 7/1992 | Gennari | 435/113 |
| 5,141,928 | 8/1992 | Goldman | 514/54 |
| 5,196,402 | 3/1993 | Braganza et al. | 514/9 |
| 5,364,845 * | 11/1994 | Henderson | 514/54 |
| 5,446,070 * | 8/1995 | Mantelle | 424/485 |
| 5,466,678 | 11/1995 | Kawabata et al. | 514/46 |
| 5,656,286 * | 8/1997 | Miranda et al. | 424/449 |
| 5,691,325 * | 11/1997 | Sandyk | 514/159 |
| 5,721,361 * | 2/1998 | Lennon et al. | 540/450 |

OTHER PUBLICATIONS

Christensen, "Nutritional Support For Injury Rehabilitation Specific Needs For The Three Phases of Rehabilitation," Chiropractic Products, pp. 100–102 (Apr. 1993).

Stramentinoli, G., "Pharmacologic Aspects of S–Adenosylmethionine," American Journal of Medicine, 83(Supp. 5A): 35–42 (1987).

Adachi et al, "The Effects of S–adenosylmethionine on Intrahepatic Cholestasis," Japan Arch. Int. Med., 33(6): 185–192 (1986).

Caruso et al, "Antidepressant Activity of S–adenosylmethionine," Lancet, 904 (1984).

Domljan et al, "A Double–blind Trail of Ademetionine vs Naproxen in Activated Gonarthrosis," Int. Journal of Clinical Pharmacology, Therapy and Toxicology, 27(7): 329–333 (1989).

Feo et al, "Early Stimulation of Polyamine Biosynthesis During Promotion by Phenobarbital of Diethylnitrosamine–induced Rat Liver Carcinogenesis: The Effects of Variations of the S–adenosyl–L–methionine Cellular Pool," Carcinogenesis, 6(12): 1713–20 (1985).

Garcea et al, "Variations of Ornithine Decarboxylase Activity and S–adenosyl–L–methionine and 5'–methylthioadenosine Contents During the Development of Diethylnitrosamine–induced Liver Hyperplastic Nodules and Hepatocellular Carcinoma," Carcinogenesis, 8 (5): 653–58 (1987).

Schumacher, "Osteoarthritis: The Clinical Picture, Pathogenesis, and Management with Studies on a New Therapeutic Agent, S–Adenosylmethionine," American Journal of Medicine, 83 (Supp. 5A): 1–4 (1987).

Frezza et al, "Oral S–Adenosylmethionine in the Symptomatic Treatment of Intrahepatic Cholestasis," Gastroenterology, 99: 211–215 (1990).

Matthews & Lewis, "The Anti–inflammatory Action of S–adenosyl–L–methionine," Pharmacol. (Life Sci. Adv.), 9: 145–152 (1990).

Szabo et al, "Sulfhydryl Compounds May Mediate Gastric Cytoprotection," Science, 214: 200–202 (Oct. 1981).

Conroy et al, "Occurrence of Ornithine Decarboxylase and Polyamines in Cartilage," Biochem. J., 162: 347–350 (1977).

Bird et al, "Putrescine—A Potent Endogenous Anti–inflammatory Substance in Inflammatory Exudates," Agents and Actions, 13: 342–347 (1983).

Oyanagui, "Anti–inflammatory Effects of Polyamines in Serotonin and Carrageenan Paw Edemata—Possible Mechanism to Increase Vascular Permeability Inhibitory Protein Level Which is Regulated by Glucocorticoids and Superoxide Radical," Agents and Actions, 14: 228–237 (1984).

Kafy et al, "In Vitro Interactions Between Endogenous Polyamines and Superoxide Anion," Agents and Actions, 18: 555–559 (1986).

Vendemiale et al, "Effects of Oral S–Adenosyl–L–Methionine on Hepatic Glutathione in Patients with Liver Disease," Scand. J. Gastroenterol., 24: 407–415 (1989).

Kaye et al, "Metabolism of Exogenous S–Adenosyl–L–Methionine in Patients with Liver Disease," Drugs, 40 (Supp. 3): 124–138 (1990).

"Current Therapy in Equine Medicine 2," Robinson, Editor, W.B. Saunders Co., Publisher, pp. 402–403 (1987).

Joosten et al, "Metabolic Evidence That Deficiences of Vitamin B–12 (Cobalamin), Folate, and Vitamin B–6 Occur Commonly in Elderly People," Am. J. Clin. Nutr., 58: 468–76 (1993).

Chen and Whanger, "Effect of Vitamin B–12 Status on Selenium Methylation and Toxicity in Rats: In Vivo and In Vitro Studies," Toxicology and Applied Pharmacology, 118: 65–72 (1993).

Drovanti et al, "Therapeutic Activity of Oral Glucosamine Sulfate in Osteoarthrosis: A Placedbo–Controlled Double–Blind Investigation," Clinical Therapeutics, 3 (4): 260–272 (1980).

Karzel and Domenjoz, "Effects of Hexosamine Derivatives and Uronic Acid Derivatives on Glycosaminoglycane Metabolism of Fibroblast Cultures," Pharmacology 5: 337–345 (1971).

Setnikar et al, "Pharmacokinetics of Glucosamine in the Dog and in Man," Arzneim.–Forsch., 36 (I): 729–735 (1986)

Anon., "Using a Chondroprotective Drug in Treating Dogs with Osteochondrosis," Veterinary Medicine, 130 (Feb. 1993).

Bucci, "Managanese: Its Role in Nutritional Balance," Today's Chirop., 17 (2): 23–28, 44 (1988).

Garrison, Jr., et al, "The Nutrition Desk Reference," Keats Publishing, Inc., pp. 70–71 (1985).

Champe et al, Lippincott's Illustrated Reviews: Biochemistry, pp. 148–50 (2nd ed. 1994).

Bucci, "Nutrition Applied to Injury Rehabilitation and Sports Medicine," CRC Press, Inc. (1994).

Hardingham et al, "Proteoglycans: Many Forms and Many Functions," 6 FASEB J. 861, 862 (1992).

Banks, "Applied Veterinary Histology," Williams and Wilkins Publisher, pp. 84–85 (1986).

Bucci, "Glucosamine—A New Potent Nutraceutical for Connective Tissues," Nutritional Supplement Advisor (Jul. 1992).

Bucci, "Chondroprotective Agents Glucosamine Salts and Chondroitin Sulfates," Townsend Letter for Doctors, pp. 52–54 (Jan. 1994).

McGarrity et al, "Effect of Selenium on Growth, S–Adenosylmethionine and Polyamine Biosynthesis in Human Colon Cancer Cells," Anticancer Research, 13: 811–815 (1993).

Dausch et al, "Increased Levels of S–Adenosylmethionine in the Livers of Rats Fed Various Forms of Selenium," Nutrition and Cancer, 20(1): 31–39 (1993).

Kajander et al, "Effects of Selenomethionine on Cell Growth and on S–adenosylmethionine Metabolism in Cultured Malignant Cells," Biochem. J., 267: 767–774 (1990).

"S–Adenosylmethionine"; *Arthritis Network*: Third Edition, Aug. 1998, 9–10.

Bassleer C., Henrotin Y., Franchimont, P., "In–Vitro Evaluation of Drugs Proposed as Chondroprotective Agents", *Int. J. Tiss Reac.*, 14 [5] (1992) 231–241.

Calia, Kurt Geoffrey; Cover Letter to USPTO with Jan. 11, 1996 date stamp indicating receipt of Petition to Make Special and the documentation in support of that petition; pp. 1–2.

Calia, Kurt Geoffrey; Petition to Make Special; Jan. 11, 1996; pp. 1–2.

Henderson, Robert J.; Declaration by Applicant in Support of Petition to Make Special ; Jan. 2, 1996; pp. 1–5, Exhibits A, B, C, and D.

Calia, Kurt Geoffrey; Declaration by Attorney in Support of Petition to Make Special; Jan. 11, 1996; pp. 1–3.

Moskowitz, Roland W., "Primary Osteoarthritis: Epidemiology; Clinical Aspects and General Management," Osteoarthritis: The Clinical Picture, Pathogenesis, and Management with Studies on a New Therapeutic Agent, S–Adenosylmethionine, The American Journal of Medicine, vol. 83(5A), Nov. 20, 1987 at 5.

Fassbender, Hans G., "Role of Chondrocytes in the Development of Osteoarthritis," Osteoarthritis: The Clinical Picture, Pathogenesis, and Management with Studies on a New Therapeutic Agent, S–Adenosylmethionine, The American Journal of Medicine, vol. 83(5A), Nov. 20, 1987 at 17.

Bassleer, Corrinne, et al., Proteoglycans Synthesized by Human Chondrocytes Cultivated in Clusters, Osteoarthritis: The New Clinical Picture, Pathogenesis, and Management with Studies on a New Therapeutic Agent, S–Adenosylmethionine. The American Journal of Medicine, vol. 83 (5A), Nov. 20, 1987 at 25.

Brandt, Kenneth D., Effects of Nonsteroidal Anti–Inflammatory Drugs on Chondrocyte Metabolism in Vitro and in Vivo. Osteoarthritis: The New Clinical Picture, Pathogenesis, and Management with Studies on a New Therapeutic Agent. S–Adenosylmethionine, The American Journal of Medicine, vol. 83 (5A), Nov. 20, 1987 at 29.

Laudanno, Oscar M., "Cytoprotective Effect of S–Adenosylmethionine Compared with That of Misoprostol against Ethanol–, Aspirin–, and Stress–Induced Gastric Damage," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 43.

Harmand, Marie–Francoise, et al., "Effects of S–Adenosylmethionine on Human Articular Chondrocyte Differentiation: An in Vitro Study," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 48.

Barcelo, Hector A., "Effect of S–Adenosylmethionine on Experimental Osteoarthritis in Rabbits," Osteoarthritis: The New Clinical Picture, Pathogenesis, and Management with Studies on a new Therapeutic Agent, S–Adenosylmethionine, The American Journal of Medicine, vol. 83 (5A), Nov. 20, 1987 at 55.

Di Padova, Carlo, "S–Adenosylmethionine in the Treatment of Osteoarthritis: Review of the Clinical Studies," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 60.

Caruso, Innocenzo, et al., "Italian Double–Blind Multicenter Study Comparing S–Adenosylmethionine, Naproxen, and Placebo in the Treatment of Degenerative Joint Disease," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 66.

Maccagno, Armando, et al., "Double–Bind Controlled Clincial Trial of Oral S–Adenosylmethionine versus Piroxicam in Knee Osteoarthritis," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 72.

Vetter, Georg, "Double–Blind Comparative Clinical Trial with S–Adenosylmethionine and Indomethacin in the Treatment of Osteoarthritis," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 78.

Muller–Fassbender, H., "Double–Blind Clinical Trial of S–Adenosylmethionine versus ibuprofen in the Treatment of Osteoarthritis," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 81.

Berger, Rainer, et al., "A New Medical Approach to the Treatment of Osteoarthritis: Report of an Open Phase IV Study with Ademetionine (Gumbaral)," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 84.

Konig, Benno, "A Long–Term (Two Years) Cliinical Trial with S–Adenosylmethionine for the Treatment of Osteoarthritis," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 89.

Baldessarini, Ross J., "Neuropharmacology of S–Adenosyl–L–Methionine," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 95.

Carney, Michael W. P., et al., "S–Adenosylmethionine and Affective Disorder," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 104.

Tavoni, Antonio, et al., "Evaluation of S–Adenosylmethionine in Primary Fibromyalgia: A Double–Bline Crossover Study," Osteoarthritis: The New Clinical Picture, Pathogenesis, and Management with Studies on a New Therapeutic Agent, S–Adenosylmethionine, The American Journal of Medicine, vol. 83 (5A), Nov. 20, 1987 at 107.

McArty, M.F., "The Neglect of Glucosamine as a Treatment of Osteoarthritis—A Personal Prospective," Medical Hypotheses, (1994), 42, 323–27.

"Vetrazene" Literature, Vetraceutical Services, Inc., 1996.

Read, RA, et al., "Systemic use of pentosan polysulphate in treatment of Osteoarthritis," Journal of Small Animal Practice. 37:108–114 (1996).

Burkhardt, P., et al., "Laboratory evaluation of anti–arthritic drugs as potential chondroprotective agents," Semin. Arthritis Rhum. 17 (suppl.):3–34 (1987).

Goad, Cathryn E., et al, "Pentosan–induced thrombocytopenia: Support for an immune complex mechanism," British Journal of Hematology, 88:803–08 (1994).

Ghosh, P., et al., "Animal models of early Osteoarthritis: Their use for evaluation of potential chondroprotective agents," Agents and Actions. Suppl. 39:195–206, (1993).

Collier, S., et al., "Evaluation of effects of antiarthritic drugs on the secretion of proteoglycans by lapine chondrocytes using a novel assay procedure," Annal of Rheumatic Diseases, 48:372–381 (1989).

Francis, DJ, et al., "Pentosan polysulphate and glycosaminoglycan polysulphate stimulate the synthesis of hyaluronan in vivo," Rheumatology International, 13(2):61–4 (1993).

Ghosh, P., "Anti–rheumatic drugs and cartilage," Bailliere's Clinical Rheumatology, 2(2):309–338 (1988).

Hutadilok N., et al., "Pentosan polysulphate stimulates hyaluronate and DNA synthesis in synovial fibroblasts and partially reduces the supportive effect of hydrocortisone on fibroblast metabolism," Current Therapeutic Research 44:845–860 (1988).

Andrews, JL, et al., The interaction of pentosan polysulphate (SP54) with human neutrophil elastase and connective tissue matrix components, Chemical and Biological interactions, 47:157–73 (1983).

Rogachefsky, RA, et al., "Treatment of canine osteoarthritis with insulin–like growth factor–1 (IGF–1) and sodium pentosan polysulfate," Osteoarthritis and Cartilage, 1:105–14 (1993).

Ghosh, P., et al., "Second–Line agents in osteoarthritis," Second–Line Agents in the Treatment of Rheumatic Diseases (Marcel Dekker, Inc., New York) pp. 363–427 (1992).

Bansal, M., et al., "The effects of calcium pentosan polysulfate on inflammatory mediators in the rat air–pouch model of inflammation," Current Therapeutic Research 54(6): 714–730 (1993).

Kalbhen, DA, "Pharmacological studies on the anti–inflammatory effect of a semi–synthetic polysaccharide (pentosan polysulfate)," Pharmacology 9: 74–79 (1973).

Klocking, HP, et al., "Effect of sodium pentosan polysulphate on the thrombogenicity of prothrombin complex concentrates," Thrombosis Research, 67(1): 41–48 (1992).

Srivastave, AK, et al., "Pentosan polysulfate, a potent anti–HIV and anti–tumor agent, inhibits protein serine/threonine and tyrosine kinases," Molecular and Cellular Biochem,. 120(2):127–33 (Mar. 24, 1993).

Senthil, D., et al., "Influence of sodium pentosan polysulphate and certain inhibitors calcium oxalate crystal growth," Molecular and Cellular Biochemistry 156(1):31–5 (Mar. 9, 1996).

Hampson, SJ, et al., "Sodium pentosanpolysulphate in the management of haemorrhagic cystitis: experience with 14 patients," European Urology 25(1):40–2 (1994).

Tardy–Poncet, B., et al., "Pentosan polysulfate–induced thrombocytopenia and thrombosis," American Journal of Hematology, 45(3):252–7 (Mar. 1994).

Verbruggen,G., et al., "Intra–articular injection of pentosanpolysulphate results in increased hyaluronan molecular weight in joint fluid," Clinical and Experimental Rheumatology 10(3):249–54 (May–Jun. 1992).

Maffrand, J.P., et al., Seminar in Thrombosis and Hemostasis, "Experimental and Clinical Pharmacology of Pentosan Polysulfate," 17(2):186–198, 1991.

Boulay, JP, et al., "Medical Therapy of Osteoarthritis in Dogs," Vet. Exchange, 17:1–20 (1995).

Bucci, LR, "Trace minerals," Nutrition Applied to Injury Rehabilitation and Sports Medicine (CRC Press Inc.. Boca Raton, FL) p. 144 (1995).

Capretto, C., et al., "A Double–Blind controlled study of S–adenosylmethionine (SAMe) v. Ibruprofen in gonarthrosis, coxarthrosis and spondylarthrosis," Clinical Trials Journal, 22(1): 15–24 (1985).

Caruso, I., et al., "Double–blind study of S–Adenosyl–methionine versus placebo in hip and knee arthrosis" Biological Methylation and Drug Design Experimental and Clinical Role of S–adenosylmethionine, Brochardt, RT, Creveling, CR, Ueland, PM, eds.(Humana Press, Clifton, NJ) (1986).

Feo, Fe., et al., "The variations of S–adenosyl–L–methionine content modulate hepatocyte growth during phenobarbital promotion of diethylnitrosamine–induced rat liver carcinogenesis," Toxicologic Pathology, 15(1):109–114 (1987).

Garcea, R., et al., "Inhibition of promotion and persistent nodule growth by S–Adenosyl–L–methionine in rat liver carcinogenesis: role of remodeling and apoptosis," Cancer Research, 49:1850–1856 (1989).

Giulidori, P., et al., "Transmethylation, transsulfuration and aminopropylation reactions of S–adenosyl–L–methionine in vivo," J Biol Chem, 259(7):4205–4211 (1984).

Gloriso, S., et al., "Double–blind multicentre study of the activity of S–adenosylmethionine in hip and knee osteoarthritis," Int J Clin Pharm Res, V(1):39–49 (1985).

Hanson, RR, "Mode of action of oral chondroprotective agents in equine practice," Equine Practice, 17(9):19 (1995).

Marcolongo, R., et al., "Double–blind multicentre study of the activity of S–Adenosyl–methionine in hip and knee osteoarthritis," Current Therapeutic Research, 37(1):82–94 (1985).

Vendemiale, G., et al., "Effects of oral S–adenosyl–L–methionine on hepatic glutathione in patients with liver disease," Scand J Gastroenterol, 24:407–415 (1989).

H. Ralph Schumacher, Jr., "Crystals, Inflammation, and Osteoarthritis," Osteoarthritis: The New Clinical Picture, Pathogenesis, and Management with Studies on a New Therapeutic Agent, S–Adenosylmethionine, The American Journal of Medicine, vol. 83(5A), Nov. 20, 1987 at 11.

* cited by examiner

AMINOSUGAR, GLYCOSAMINOGLYCAN, AND S-ADENOSYLMETHIONINE COMPOSITION FOR THE TREATMENT AND REPAIR OF CONNECTIVE TISSUE

CROSS-REFERENCE TO RELATED APPLICATION

The present application is a continuation-in-part of co-pending U.S. patent application Ser. No. 08/779,996, filed Dec. 23, 1996, the disclosure of which is incorporated by reference herein in its entirety.

BACKGROUND OF THE INVENTION

1. Field of the Invention

The present invention relates to compositions for the repair and reduction of inflammation of connective tissue in humans and animals and, in particular, to compositions capable of promoting anti-inflammation, chondroprotection, chondromodulation, chondrostabilization, chondrometabolization and the repair and replacement of human and animal connective tissue.

2. Background of the Invention

The connective tissues of humans and animals are constantly subjected to stresses and strains from mechanical forces and from diseases that can result in afflictions, such as arthritis, joint inflammation and stiffness. Indeed, connective tissue afflictions are quite common, presently affecting millions of Americans. Further, such afflictions can be not only painful but, in their extreme, debilitating.

The treatment of connective tissue afflictions can be quite problematic. A simple decrease in the stress to which the connective tissue is subjected is often not an option, especially in the case of athletes and animals such as race horses. Consequently, treatment is often directed at controlling the symptoms of the afflictions and not their causes, regardless of the stage of the degenerative process.

Presently, steroids, such as corticosteroids and NSAIDs, are widely used for the treatment of these ailments. [Vidal, et al., *Pharmocol. Res. Commun.*, 10:557–569 (1978)]. However, drugs such as these, which inhibit the body's own natural healing processes, may lead to further deterioration of the connective tissue.

Connective tissue, for example articular cartilage, is naturally equipped to repair itself by manufacturing and remodeling prodigious amounts of collagen (a chief component of connective tissue such as cartilage) and proteoglycans (PGs) (the other major component of connective tissue such as cartilage). This ongoing process is placed under stress when an injury occurs. In such cases, the production of connective tissue matrix (collagen and PGs) can double or triple over normal levels, thereby increasing the demand for the building blocks of both collagens and proteoglycans.

The building blocks for collagen are amino acids, especially proline, glycine and lysine. PGs are large and complex macromolecules comprised mainly of long chains of modified sugars called glycosaminoglycans (GAGs) or mucopolysaccharides. The terms GAGs and mucopolysaccharides are understood in the art to be interchangeable. PGs provide the framework for collagen formation and also hold water to give flexibility, resiliency and resistance to compression.

Like almost every biosynthetic pathway in the body, the pathways by which both collagen and GAG form single molecule precursors are quite long. As is also characteristic of other biosynthetic pathways, the pathways by which collagen and GAGs are produced include what is called a rate-limiting step—that is, one highly regulated control point beyond which there is a commitment to finish. The presence of such rate-limiting steps permits complicated biosynthetic processes to be more easily and efficiently controlled by permitting the organism to focus on one point. For example, if conditions demand production and all the requisite raw materials are in place, then stimulation of the rate-limiting step will cause the end product to be produced. To stop or slow production, the organism needs simply to regulate the rate-limiting step.

In the production of PGs, the rate-limiting step is the conversion of glucose to glucosamine for the production of GAGs. Glucosamine, an aminosugar, is the key precursor to all the various modified sugars found in GAGs, including glucosamine sulfate, galactosamine, N-acetylglucosamine, etc. Glucosamine also makes up to 50% of hyaluronic acid—the backbone of PGs—on which other GAGs, like chondroitin sulfate are added. The GAGs are then used to build PGs and, eventually, connective tissue. Once glucosamine is formed, there is no turning away from the synthesis of GAG polymers.

Glucosamine has been shown to be rapidly absorbed into humans and animals after oral administration. A significant portion of the ingested glucosamine localizes to cartilage and joint tissues, where it remains for long periods. This indicates that oral administration of glucosamine reaches connective tissues, where glucosamine is incorporated into newly-synthesized connective tissue.

Glycosaminoglycans and collagen are the chief structural elements of all connective tissues. Their synthesis is essential for proper maintenance and repair of connective tissues. In vitro, the introduction of glucosamine has been demonstrated to increase the synthesis of collagen and glycosaminoglycans in fibroblasts, which is the first step in repair of connective tissues. In vivo, topical application of glucosamine has enhanced wound healing. Glucosamine has also exhibited reproducible improvement in symptoms and cartilage integrity in humans with osteoarthritis. [L. Bucci, *Nutritional Supplement Advisor*, (July 1992)].

The pathway for the production of proteoglycans may be briefly described as follows. Glucosamine is the main building block of connective tissue and may be provided either through the enzymatic conversion of glucose or through diet or external administration (see FIG. 1). Glucosamine may be converted into the other main component of connective tissue, namely PGs, upon incorporation of glucosamine into GAGs (see FIG. 2).

More specifically, GAGs are large complexes of polysaccharide chains associated with a small amount of protein. These compounds have the ability to bind large amounts of water, thereby producing a gel-like matrix that forms the body's ground substance. GAGs stabilize and support cellular and fibrous components of tissue while maintaining the water and salt balance of the body. The combination of insoluble protein and the ground substance forms connective tissue. For example, cartilage is rich in ground substance while tendon is composed primarily of fibers.

GAGs are long chains composed of repeating disaccharide units of monosaccharides (aminosugar-acidic sugar repeating units). The aminosugar is typically glucosamine or galactosamine. The aminosugar may also be sulfated. The acidic sugar may be D-glucuronic acid or L-iduronic acid. GAGs, with the exception of hyaluronic acid, are covalently bound to a protein, forming proteoglycan monomers. These PGs consist of a core protein to which linear carbohydrate chains formed of monosaccharides are attached. In cartilage proteoglycan, the species of GAGs include chondroitin sulfate and keratin sulfate. The proteoglycan monomers then associate with a molecule of hyaluronic acid to form PG aggregates. The association of the core protein to hyaluronic acid is stabilized by link proteins.

The polysaccharide chains are elongated by the sequential addition of acidic sugars and aminosugars, and the addition is catalyzed by a family of transferases. Aminosugars, such as glucosamine, are synthesized through a series of enzymatic reactions that convert glucose to glucosamine, or alternatively may be provided through the diet. The glucosamine is then incorporated into the GAGs as described above. Acidic sugars may be provided through the diet, may be obtained through degradation of GAGs by degradative enzymes, or produced through the uronic acid pathway.

Figure 1:
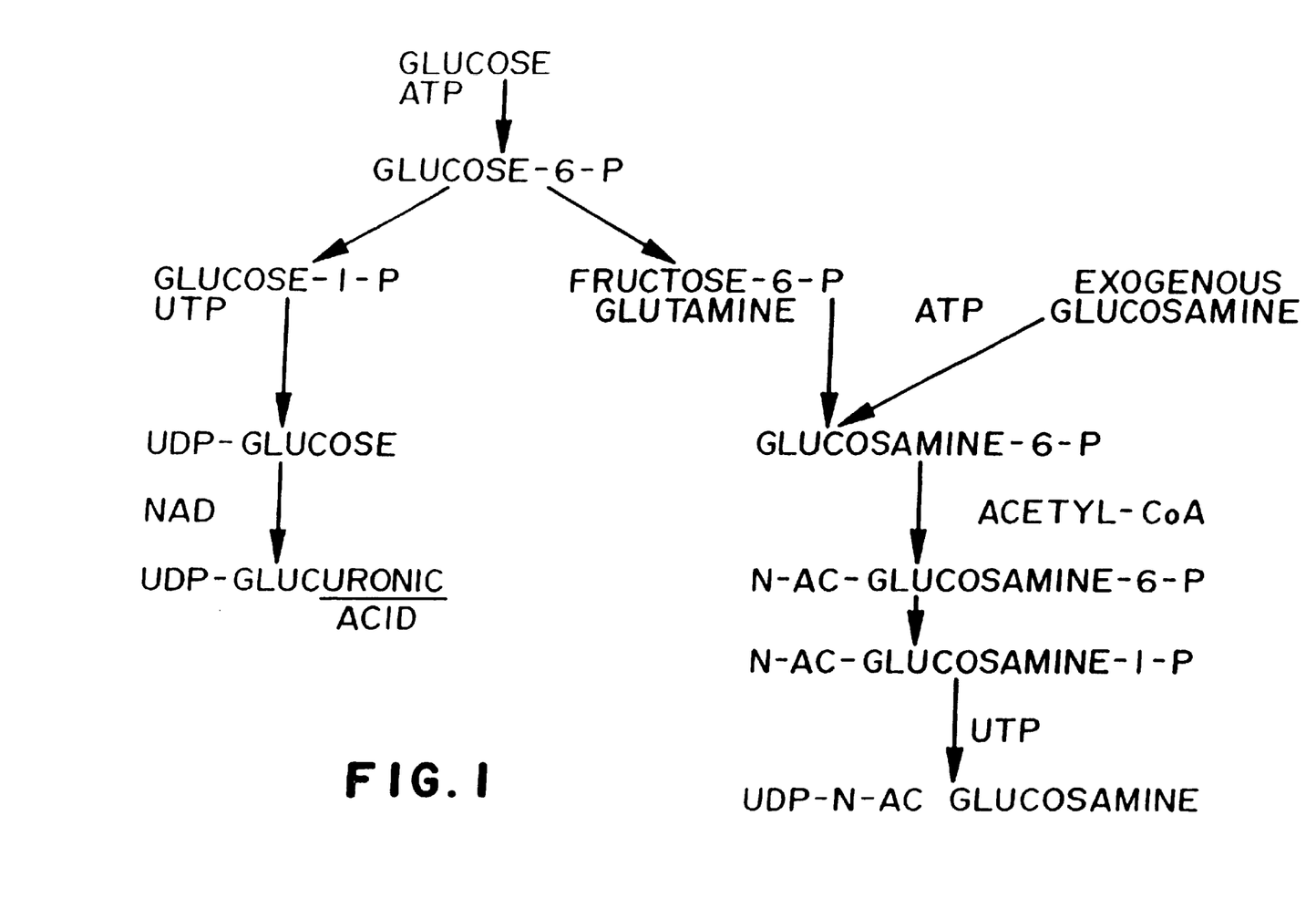
FIG. 1 is a sequence for the biosynthesis of hexosamines.

Since repeating disaccharide units contain one aminosugar (such as glucosamine), it is clear that the presence of an aminosugar in the production of connective tissue is important. Glucosamine is, by far, the more important ingredient in the production of connective tissue since it is the essential building block of GAGs. See FIG. 1. All GAGs contain hexosamine or uronic acid derivative products of the glucose pathway and from exogenous glucosamine, for example:

| | |
|---|---|
| Hyaluronic acid | Glucosamine + Glucuronic Acid |
| Keratan-Sulfate | Glucosamine + Galactose |
| Chondroitin Sulfate | Glucuronic Acid + Galactosamine |
| Heparin Sulfate | Glucosamine + Glucuronic or Iduronic Acid |
| Heparan Sulfate | Glucosamine + Glucuronic or Iduronic Acid |
| Dermatin Sulfate | Iduronic Acid + Galactosamine |

Chondroitin sulfate is a GAG that provides a further substrate for the synthesis of the proteoglycans. The provision of the chondroitin in its salt (sulfate) form facilitates its delivery and uptake by the humans and animals in the production of connective tissue. In addition, the sulfate portion of chondroitin sulfate is available for use in catalyzing the conversion of glucosamine to GAGs. Fragments of GAGs, including chondroitin sulfate, may also be used to provide a substrate for synthesis of proteoglycans since the assembly of PG occurs in the extracellular space.

In addition, chondroitin sulfate has been shown to have cardiovascular health benefits. [Morrison et al., *Coronary Heart Disease and the Mucopolysaccharides (Glycosaminoqlycans)*, pp. 109–127 (1973)]. Thus, the preferred form of glycosaminoglycan included in the compositions of the present invention is chondroitin sulfate or fragments thereof.

Chondroitin may be more efficacious than glucosamine for injury rehabilitation. [Christensen, *Chiropractic Products*, pp. 100–102 (April 1993)]. An evaluation of glucosamine versus chondroitin for treatment of osteoarthritis has been conducted and concludes, contrary to Christensen, that glucosamine is preferred. [Murray, *MPI's Dynamic Chiropractic*, pp. 8–10 (Sep. 12, 1993)]. Neither reference teaches or suggests combining the materials. Bucci (*Townsend Letter for Doctors*, pp. 52–54, January 1994), discloses the combination of glucosamine and chondroitin for treatment of osteoarthritis. Bucci has acknowledged that this combination was personally disclosed to him by one of the present inventors.

Chondroitin sulfate also acts to inhibit the degradative enzymes that break down connective tissue. In so doing, chondroitin sulfate promotes the maintenance of healthy connective tissues. When combined with glucosamine, which functions primarily as a building block for the synthesis of connective tissue, chondroitin sulfate works in concert with the glucosamine but may work in a different fashion. The ability of chondroitin sulfate to block degradation is one of its important functions.

S-Adenosylmethionine (SAM) is a significant physiologic compound which is present throughout body tissue and takes part in a number of biologic reactions as a methyl group donor or as an enzymatic activator during the synthesis and metabolism of hormones, neurotransmitters, nucleic acids, phospholipids, and proteins. SAM may be second only to adenosine triphosphate (ATP) in the variety of reactions in which it is a cofactor. SAM is metabolized via three metabolic pathways of transmethylation, transsulfuration, and aminopropylation. [Stramentinoli, *Am. J. Med.*, 83(5A) :35–42 (1987)]. In higher organisms, SAM plays a significant role in transmethylation processes with more than 40 anabolic or catabolic reactions involving the transfer of the methyl group of SAM to substrates such as nucleic acids, proteins, and lipids, among others. Also, the release of the methyl group from SAM is the start of a "transsulfuration" pathway that produces all endogenous sulfur compounds. After donating its methyl group, SAM is converted into S-adenosylhomocysteine, which in turn is hydrolyzed to adenosine and homocysteine. The amino acid cysteine may then be produced from the homocysteine. The cysteine thus produced may exert a reducing effect by itself or as an active part of glutathione, which is a main cell anti-oxidant. [Stramentoli, cited above].

SAM has been used to treat various disorders. In various forms of liver disease, SAM acts as an anticholestatic agent. [Adachi et al., *Japan Arch. Inter. Med.*, 33:185–192 (1986)]. SAM has also been administered as an antidepressant for use in the management of psychiatric disorders [Caruso et al., *Lancet*, 1: 904 (1984)], and as an anti-inflammatory compound in the management of osteoarthritis [Domljan et al., *Int. J. Clin. Pharm. Toxicol.*, 27(7):329–333 (1989)].

Low levels of SAM are believed to play a role in reducing the risk of certain cancers. [Feo et al., *Carcinogenesis*, 6:1713–20 (1985)]. In addition, the administration of SAM has also been associated with a fall in the amount of early reversible nodules and the prevention of the development of late pre-neoplastic lesions and hepatocellular carcinomas. [Garcea et al., *Carcinogenesis*, 8:653–58 (1987)].

Unfortunately, SAM per se is unstable due to its high reactivity. The relatively recent synthesis of stable salts, however, has made SAM available for research and therapeutic use. [See, e.g., U.S. Pat. Nos. 4,990,606 and 5,102, 791].

SAM has been used outside of the United States in a number of clinical trials concerning the treatment of osteoarthritis. While used in these trials primarily as an analgesic and replacement for NSAID therapy, SAM is a precursor of polyamines. In addition to their analgesic and anti-inflammatory properties, and their ability to scavenge free radicals, polyamines may stabilize the polyanionic macromolecules of proteoglycans. [Schumacher, *Am. J. Med.*, 83(5A):2 (1987)].

SAM may also function as a source of endogenous sulfur, which will increase sulfation of GAGs to be incorporated in proteoglycans. The inclusion of SAM is particularly beneficial in instances of subclinical deficiencies of SAM, occurring especially in elderly populations with higher risk of osteoarthritis [Frezza et al., *Gastroenterol.*, 99:211–215

(1990)]. The supplementation of SAM may aid in instances of SAM deficiency where the ability of the body to sulfate GAGs may be compromised.

In addition, a number of metabolites of SAM aid in the repair of connective tissue, including glutathione, polyamines, methylthioadenosine, and adenosine. Glutathione works as a scavenger of oxygen-related products [Shumacher, *Am. J. Med.*, 83(Supp 5a):1–4 (1987); Matthew & Lewis, *Pharmacol. (Life Sci. Adv.)*, 9:145–152 (1990); Szabo et al., *Science*, 214:200–202 (1981)] and thus has an anti-inflammatory effect. Polyamines, including spermine, spermidine, and putrescine, stabilize polyanionic macromolecules of proteoglycans [Schumacher, cited above; Conroy et al., *Biochem. J.*, 162:347–350 (1977)] and thus protect proteolytic and glycolytic enzymes. These polyamines also have an anti-inflammatory effect [Bird et al., *Agents Actions*, 13:342–347 (1983); Oyangui, *Agents Actions*, 14:228–237 (1984)], probably as a scavenger of oxygen-related products [Kafy et al., *Agents Actions*, 18:555–559 (1986); Matthews & Lewis, cited above], and have an analgesic effect [Bird et al., cited above; Oyangui, cited above]. The SAM metabolite methylthioadenosine has a pronounced anti-inflammatory effect [Matthews & Lewis, 1990] while adenosine has a more modest anti-inflammatory effect [Matthews & Lewis, 1990].

Studies have shown that some forms of exogenous SAM are stable in digestive juices when given orally. [Stramentinoli et al., cited above; Vendemiale et al., *Scand. J. Gastroenterol.*, 24:407–415 (1989)]. The metabolism of exogenous SAM appears to follow known pathways of endogenous SAM metabolism. [Kaye et al., *Drugs*, 40 (Suppl. 3):124–138 (1990)]. In humans, oral SAM was tolerated to the same extent as placebo with very mild nonspecific side effects. [Schumacher, cited above; Frezza et al., cited above].

Manganese plays a role in the synthesis of GAGs, collagen and glycoproteins which are important constituents of cartilage and bone. Manganese is important for enzyme activity of glycosyltransferases. This family of enzymes is responsible for linking sugars together into glycosaminoglycans, adding sugars to other glycoproteins, adding sulfate to aminosugars, converting sugars into other modified sugars, and adding sugars to lipids. The enzymatic functions of glycosyltransferases are important in glycosaminoglycan synthesis (hyaluronic acid, chondroitin sulfate, keratan sulfate, heparin sulfate and dermatin sulfate, etc.), collagen synthesis, and in the functions of many other glycoproteins and glycolipids.

Manganese also plays a role in the synthesis of glycosaminoglycans and glycoproteins, which are important constituents of cartilage and bone. Many reproductive problems in horses and skeletal abnormalities in foals have been ascribed to manganese deficiency. [*Current Therapy in Equine Medicine*, 2:402–403 (1987)].

Manganese deficiency leads to abnormal bone growth, swollen and enlarged joints, and slipped tendons in humans and animals. In humans, manganese deficiencies are also associated with bone loss and arthritis. Levels of all glycosaminoglycans are decreased in connective tissues during manganese deficiencies, with chondroitin sulfates being most depleted. Manganese-deficient organisms quickly normalize glycosaminoglycans and collagen synthesis when manganese is replenished.

Approximately 40% of dietary manganese is absorbed by the body tissue. Storage of manganese in the body is minimal—a mere 12 to 20 mg is present in the body at any one time. Large amounts of calcium and phosphorus in the intestine are also known to interfere with manganese absorption. The richest dietary sources are the foods least consumed by the general public, such as whole grain cereals and breads, dried peas, beans and nuts. The ascorbate form of manganese is preferred due to the high bioavailability and the need for vitamin C (ascorbic acid) for collagen production. Vitamin C also enhances manganese uptake by the body.

Other optional ingredients in the compositions of the present invention are methyl donors or methyl donor cofactors, such as vitamins B12 and B6, folic acid, dimethylglycine, and trimethylglycine. These ingredients augment the function of SAM in that they are cofactors in methylation. In addition, these compounds are likely to be lacking in patients suffering from connective tissue disorders. For example, it is estimated that 12% of the elderly population in the United States suffers from a vitamin B12 deficiency, a group more likely to suffer from connective tissue disorders.

An adequate amount of vitamin B12, for example, has an important environmental influence on the accumulation of homocysteine that results from the metabolism of SAM. In other words, methyl donors or methyl donor cofactors, such as vitamin B12 and the others listed in the preceding paragraph, can reduce levels of homocysteine when administered either alone or in combination.

Vitamin B12 is generally known to function as a coenzyme in biochemical reactions such as the synthesis of proprionic acid and of methionine. Recent evidence suggests that the elevated levels of plasma homocysteine increase the risk of occlusive vascular disease. Adequate amounts of vitamin B12 are considered the most important environmental influence on the accumulation of unnecessary homocysteine. [Joosten et al., *Am. J. Clin. Nutr.*, 58(4): 468–76 (1993)]. In addition, it is also understood that vitamin B12 may play a role in the methylation of selenium. [Chen and Whanger, *Tox. and Appl. Pharm.*, 118:65–72 (1993)]. Specifically, increased levels of vitamin B12 significantly contribute to selenium methylation and might decrease overall selenium toxicity by preventing its accumulation in tissues. [Chen and Whanger, cited above].

3. Description of Background Art

Several disclosures suggest provide exogenous quantities of glucosamine in order to bypass the rate-limiting step of the conversion of glucose to glucosamine in those pathways that produce PGs. For example, the intravenous administration of glucosamine (a precursor of the GAGs) and derivatives thereof has been disclosed in U.S. Pat. No. 3,232,836, issued to Carlozzi et al., for assisting in the healing of wounds on the surface of the body. In U.S. Pat. No. 3,682,076, issued to Rovati, the use of glucosamine and salts thereof is disclosed for the treatment of arthritic conditions. Finally, the use of glucosamine salts has also been disclosed for the treatment of inflammatory diseases of the gastrointestinal tract in U.S. Pat. No. 4,006,224 issued to Prudden. In vitro, glucosamine increases syntheses of collagen and glycosaminoglycans, the first step in repair of connective tissues, in fibroblasts. In vivo, topical application of glucosamine has enhanced wound healing.

Several disclosures also suggest going one step further in bypassing the glucose-to-glucosamine rate-limiting step, by providing exogenous quantities of various of the modified sugars found in the GAGs for producing proteoglycans. For example, in U.S. Pat. No. 3,6797,652 issued to Rovati et al., the use of N-acetylglucosamine is disclosed for treating degenerative afflictions of the joints.

In still other disclosures of which we are aware, it has been taught to go still one step further in bypassing the glucose-to-glucosamine rate-limiting step by providing exogenous quantities of the GAGs themselves (with and without various of the modified sugars). For example, in U.S. Pat. No. 3,371,012 issued to Furuhashi, a preservative is disclosed for eye graft material that includes galactose, N-acetylglucosamine (a modified sugar found in the GAGs) and chondroitin sulfate (a GAG). Additionally, U.S. Pat. No. 4,486,416 issued to Soll et al., discloses a method of protecting corneal endothelial cells exposed to the trauma of intraocular lens implantation surgery by administering a prophylactically effective amount of chondroitin sulfate. Also, U.S. Pat. No. 5,141,928 issued to Goldman discloses the prevention and treatment of eye injuries using glycosaminoglycan polysulfates.

U.S. Pat. No. 4,983,580 issued to Gibson, discloses methods for enhancing the healing of corneal incisions. These methods include the application of a corneal motor composition of fibronectin, chondroitin sulfate and collagen to the incision.

In U.S. Pat. No. 4,801,619 issued to Lindblad, the intraarticular administration of hyaluronic acid is disclosed for the treatment of progressive cartilage degeneration caused by proteoglycan degradation.

The use of a SAM and selenium composition as a nutritional supplement is disclosed in United States patent application Ser. No. 08/725,194 filed by one of the present inventors and is herein incorporated by reference. In addition, one of the inventors of the present invention has taught, in U.S. Pat. No. 5,587,363 the combination of an aminosugar, such as glucosamine, and a glycosaminoglycan, such as chondroitin, for treatment of degenerative joint diseases. One of the present inventors has further taught the optional inclusion of manganese in a composition of an aminosugar and a glycosaminoglycan in U.S. Pat. No. 5,364,845.

Accordingly, it can be seen that there remains a need for compositions which include analgesic, anti-inflammatory, and antidepressant components, as well as components that provide the building blocks for the production of connective tissue in humans and that also protect against the degradation of that tissue.

SUMMARY OF THE INVENTION

It is therefore an object of the present invention to provide a composition for the protection and repair and for reducing the inflammation of connective tissue in humans and animals.

It is a further object of the present invention to provide compositions which contain S-Adenosylmethionine and an aminosugar or salts thereof, such as glucosamine, for facilitating the repair and reducing the inflammation of connective tissue in humans and animals.

It is another object of the present invention to provide compositions which contain S-Adenosylmethionine and GAGs, such as chondroitin salts and fragments thereof, for facilitating the repair and for reducing the inflammation of connective tissue in humans and animals.

It is yet a further object of the present invention to provide compositions which contain S-Adenosylmethionine, an aminosugar or salts thereof, and GAGs or fragments thereof for facilitating the repair and for reducing the inflammation of connective tissue in humans and animals.

It is another object to optionally provide manganese to any of these compositions for humans and animals.

It is still a further object to optionally provide methyl donors or methyl donor cofactors, such as vitamins B12 and B6, folic acid, dimethylglycine, and trimethylglycine, to the compositions of the present invention for humans and animals if desirable.

It is a further object of the present invention to provide methods of administering these compositions.

These and other objects of the present invention will become readily apparent from a reading of the following detailed description and examples.

DETAILED DESCRIPTION OF THE INVENTION

According to the present invention, a composition selected from the group consisting of SAM and an aminosugar or salts thereof (e.g., glucosamine); SAM and GAGs (e.g., chondroitin salts) or fragments thereof; and SAM, an aminosugar (or salts thereof), and GAGs (or fragments thereof) is provided to humans and animals for stimulating both collagen and PG synthesis and for reducing inflammation. Manganese, preferably manganese salts, may optionally be included to any of these compositions. In addition, other optional ingredients include methyl donors or methyl donor cofactors, such as vitamins B12 and B6, folic acid, dimethylglycine, and trimethylglycine. These compositions may act to accomplish several functions, including bypassing the glucose to glucosamine rate-limiting step in the natural production of proteoglycans in humans and animals, and producing additional quantities of collagen and proteoglycans for use in the repair of damaged connective tissue. In addition, inflammation of connective tissue may be reduced by the compositions of the invention. The compositions of the present invention may achieve these functions directly or through indirect pathways—i.e., through their effect on other components in the living system which in turn can increase connective tissue synthesis or reduce inflammation.

In one embodiment, a composition of the present invention include S-Adenosylmethionine (SAM) and an aminosugar, such as glucosamine, preferably in a salt form. In another embodiment of the present invention, the composition includes SAM and a glycosaminoglycan, such as chondroitin (preferably in a salt form such as chondroitin sulfate). In another embodiment, the composition of the present invention includes SAM, an aminosugar, such as glucosamine, preferably in a salt form, and a glycosaminoglycan, such as chondroitin (preferably in a salt form, such as chondroitin sulfate). Alternatively, fragments of a glycosaminoglycan may be used in a composition of the invention in addition to or in substitution for the glycosaminoglycan. Each of these compositions may optionally include manganese. A preferred form of manganese in such compositions is a manganese salt, such as manganese ascorbate, because the ascorbate is a soluble form of manganese which further provides ascorbic acid, a substance needed for collagen synthesis. Other manganese salts such, as for example, sulfate or gluconate, may be used however. Each of these compositions may optionally contain one or more methyl donors or methyl donor cofactors selected from the group consisting of vitamins B12 and B6, folic acid, dimethylglycine, and trimethylglycine.

Figure 2:
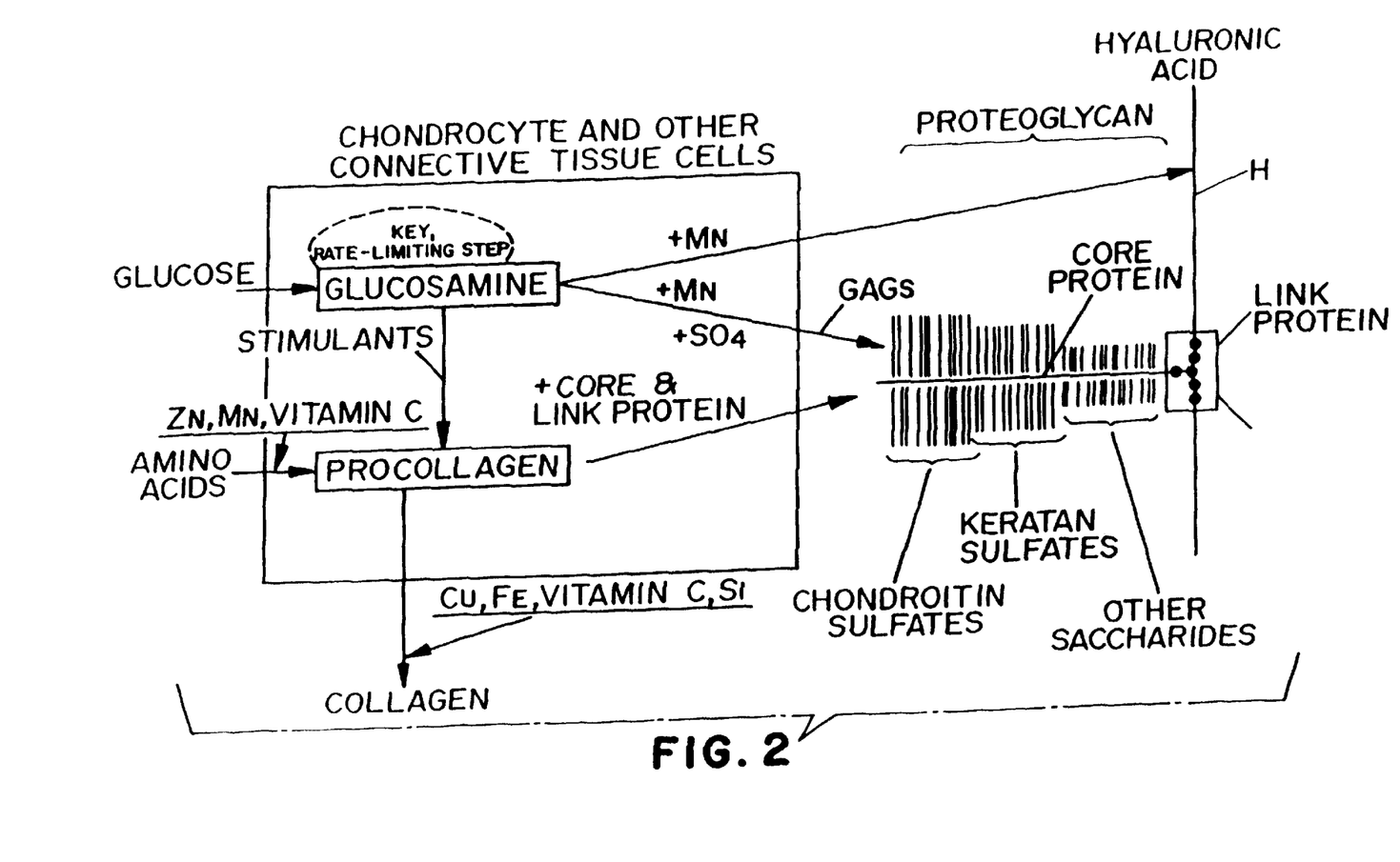
FIG. 2 is a schematic flowchart illustrating the biological pathway by which the composition of the present invention aids in protection and repair of connective tissue.
Figure 3:
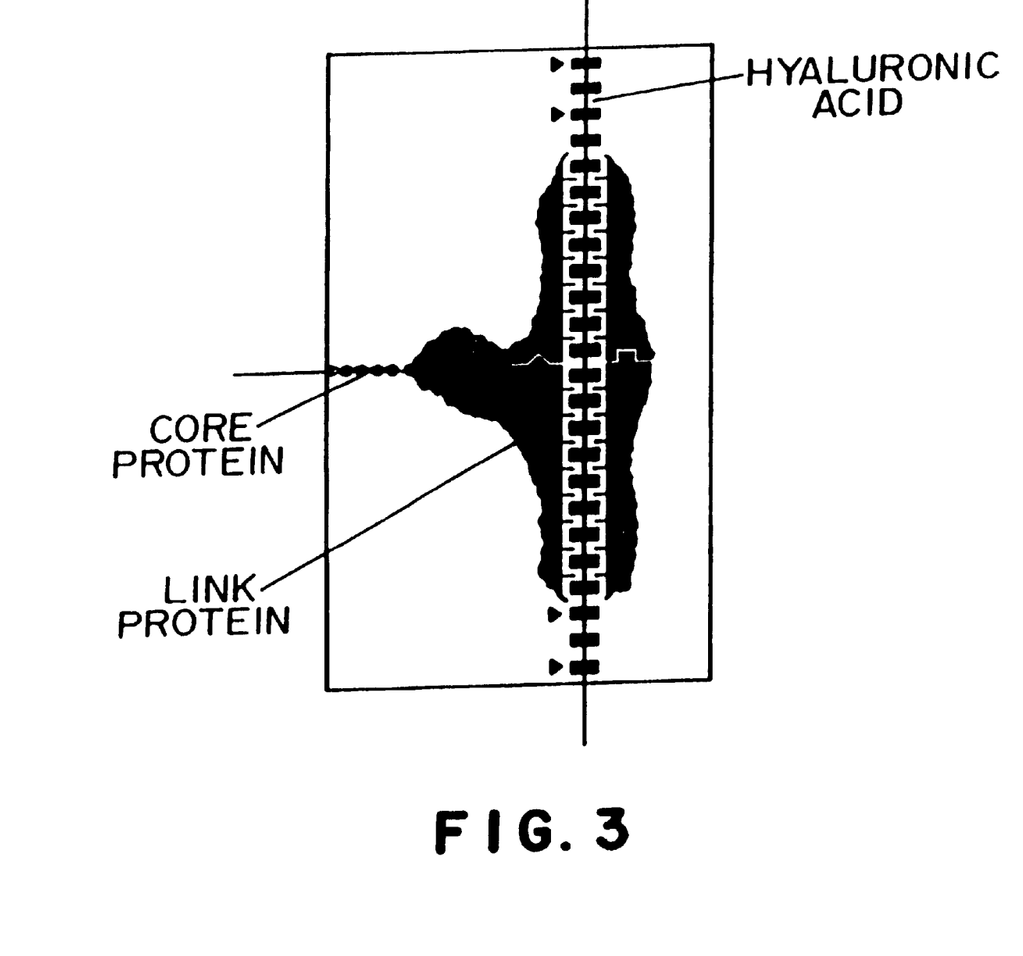
FIG. 3 is an enlarged portion of the flowchart of FIG. 2.

Referring to FIGS. 2 and 3, the biosynthetic pathway for the production of connective tissue, which is affected by the method of the present invention by virtue of the components of the composition of the present invention which aid in connective tissue repair, functions as described in the above background section of this application.

In a preferred embodiment, the aminosugar glucosamine is the base of the composition, providing the primary substrate for both collagen and proteoglycan synthesis. Glucosamine is the preferred substrate for proteoglycan synthesis, including chondroitin sulfates and hyaluronic acid. The glucosamine preferably is in a salt form so as to facilitate its delivery and uptake by humans and animals. The preferred salt forms are glucosamine hydrochloride, glucosamine sulfate and N-acetylglucosamine.

Administration of a preferred embodiment of the composition of the present invention provides the human or animal organism with exogenous quantities of SAM, an aminosugar or salts thereof, and a glycosaminoglycan or fragments thereof. If desired, the composition also provides the human or animal organism with exogenous quantities of manganese cofactors. Also if desired, the compositions of the present invention may include methyl donors or methyl donor cofactors, such as vitamins B12 and B6, folic acid, dimethylglycine, and trimethylglycine.

The exogenous glucosamine provided by the composition of present invention is converted to proteoglycans as is seen in FIG. 2 and as described above.

In the former case, the glucosamine may be converted with the aid of manganese directly into GAG, including hyaluronic acid (which is 50% glucosamine and which forms the backbone of the proteoglycans). This core protein is then linked to the hyaluronic acid via the link protein, as is seen in FIG. 3.

In the latter case, the free amino acids are, with the aid of manganese and zinc cofactors (and ascorbic acid or vitamin C), converted to procollagen. The procollagen is then converted into collagen with the aid of copper or iron cofactors and vitamin C (ascorbic acid) and sulfate chelates.

Thus, preferred compositions of the present invention containing SAM and glucosamine advantageously stimulate the synthesis of collagen and glycosaminoglycans or mucopolysaccharides (GAGs), including hyaluronic acid, the backbone of proteoglycans (PG's), thereby providing a natural tissue repair function. These compositions provide the connective tissue repair function of glucosamine, the increased sulfation of GAGs by SAM, the stabilization by SAM metabolites of the polyanionic macromolecules of proteoglycans, and the additional analgesic, anti-inflammatory, and anti-depressant effects of SAM. The optional addition of manganese provides a further benefit if a deficiency of the mineral exists or if it is otherwise desired. The optional inclusion of methyl donors or methyl donor cofactors, such as vitamins B12 and B6, folic acid, dimethylglycine, and trimethylglycine, helps to promote methylation and thereby convert homocysteine to methionine.

Another preferred composition of the invention comprises SAM and chondroitin salts (such as chondroitin sulfate). SAM operates in this composition, in conjunction with endogenous glucosamine, as described above. Chondroitin salts operate with SAM and endogenous glucosamine by inhibiting the synovial degradative enzymes. Chondroitin salts (such as chondroitin sulfate) also directly contribute to the pool of GAGs of cartilaginous tissue. Manganese salts may also be included in this composition in those cases where a deficiency of manganese exists. Methyl donors or methyl donor cofactors, such as vitamins B12 and B6, folic acid, dimethylglycine, and trimethylglycine, may optionally be included in these compositions to help promote methylation and thereby convert homocysteine to methionine.

Another preferred embodiment of the composition of the present invention contains SAM, glucosamine, and chondroitin salts (such as chondroitin sulfate) and mixtures and fragments thereof, and also advantageously stimulates the synthesis of collagen and glycosaminoglycans or mucopolysaccharides (GAGs), including hyaluronic acid, thereby providing a natural tissue repair function. This composition provides the superior connective tissue repair function of glucosamine, the above-described benefits of SAM, and the above-described benefits from chondroitin salts (including chondroitin sulfate) and fragments of chondroitin salts. Chondroitin salts (including chondroitin sulfate) also operate with SAM and glucosamine by inhibiting the synovial degradative enzymes. Chondroitin salts (including chondroitin sulfate) also directly contribute to the pool of GAGs of cartilaginous tissue. Manganese provides a further benefit if a deficiency of the mineral exists. As with the compositions described above, methyl donors or methyl donor cofactors, such as vitamins B12 and B6, folic acid, dimethylglycine, and trimethylglycine, may optionally be included in these compositions to help promote methylation and thereby convert homocysteine to methionine. Tissue repair can thus be accomplished, in the context of the treatment and repair of connective tissue and the treatment of arthritic conditions, in almost all areas of the body both human and animal.

In the present method for the treatment and repair and for reducing the inflammation of connective tissue in humans and animals, preferred compositions comprising amounts of SAM in combination with glucosamine including salts thereof in combination with chondroitin salts (including chondroitin sulfate) or fragments thereof, or amounts of SAM and chondroitin salts (including chondroitin sulfate) or fragments thereof in combination with glucosamine including salts thereof, may be administered to humans and animals thereof for stimulating both collagen and proteoglycan synthesis. An additional preferred composition comprising amounts of SAM and chondroitin salts (including chondroitin sulfate) or fragments thereof may be administered to humans and animals for stimulating proteoglycan synthesis and reducing inflammation. Manganese salts may also be optionally included in each composition in cases where a deficiency of manganese exists. Methyl donors or methyl donor cofactors, such as vitamins B12 and B6, folic acid, dimethylglycine, and trimethylglycine may optionally be included to these compositions as well.

The compositions of the present invention are administered to promote tissue repair, including cartilage repair, and the treatment of arthritic conditions as well as connective tissue damage in humans and animals. The anti-depressant effect of SAM may help to alleviate the burden of sickness for some patients, thus enhancing their quality of life. This effect, as well as the analgesic and anti-inflammatory effects of SAM which will help alleviate the pain associated with arthritic conditions, may help remove impediments to physical activity. Increased levels of physical activity, in turn, can supply the loading and unloading forces necessary for the regeneration of articular cartilage. Supplementation with glucosamine, with its chondroprotective role, thus helps to ensure that the raw materials are available to support the increased regeneration of cartilage. The compositions of the present invention are also understood to play a role in chondromodulation, chondrostabilization, and chondrometabolizaton.

The dosage of SAM in the nutritional supplements of the present invention ranges from about 5 mg to about 5,000 mg in humans and small animals, and from about 2 mg to about 20,000 mg in large animals (e.g., equine). The dosage of glucosamine in the nutritional supplements of the present invention ranges from about 50 mg to about 5,000 mg in humans and small animals, and from about 250 mg to about 40,000 mg in large animals (e.g., equine). The dosage of chondroitin salts in the nutritional supplements of the present invention ranges from about 15 mg to about 5,000 mg in humans and small animals, and from about 100 mg to about 30,000 mg in large animals. When included in the compositions of the present invention, manganese may optionally be present in the range of about 2 to about 75 mg in humans and small animals, and from about 10 mg to about 500 mg in large animals. The ascorbate component of the manganese ascorbate may range from about 10 mg to about 500 mg in humans and small animals, and from about 50 mg to about 2,500 mg in large animals. When included in the compositions of the present invention, the methyl donors or methyl donor cofactors, such as vitamins B12 and B6, folic acid, dimethylglycine, and trimethylglycine may be present in the range of about 0.1 mg to about 10 mg in humans and small animals, and from about 1 mg to about 100 mg in large animals.

As a preferred embodiment, a dosage of the nutritional supplement composition of the present invention may consist of one or more capsules or tablets for human oral consumption. In such an embodiment, the preferred weight of the dosage is between about 5 mg to about 5,000 mg, and preferably about 2,500 mg. The dosage may be administered in a single daily dosage form in which all components are present, e.g., a capsule or tablet of preferably 2,500 mg. The dosage may also be administered in more than one dosage form in which each dosage form contains at least one component. When a single dosage is administered in more than one dosage form, the multiple dosage forms may be co-administered as a single dosage. Thus, for example, a single dosage may be comprised of a SAM dosage form co-administered with a glucosamine and chondroitin salts dosage form.

Alternatively, the nutritional supplement compositions of the present invention may be administered more than once daily. Hence, for example, the nutritional supplement compositions of the present invention may be in the form of an oral dosage form of 1250 mg administered twice daily or 833 mg administered three times daily. The number of daily administrations will depend upon the needs of the human or animal recipient. Different connective tissue disorders and injuries require different amounts of the compositions of the present invention. In that regard, several dosages may be administered depending on the particular needs of the human or animal.

Alternatively, and of particular use in large animals, the compositions of the present invention may for example be administered in scoops. Such administration may take the form, for example, of a level scoopful containing about 1,800 mg glucosamine, about 600 mg chondroitin salts, about 16 mg of manganese (when included in the form of manganese ascorbate), and about 104 mg of ascorbate (when included in the form of manganese ascorbate).

These preparations may be made by conventional methods. For example, to prepare the compositions of the invention, the above-described ingredients are combined as the active ingredient in intimate admixture with a suitable carrier according to conventional compounding techniques. This carrier may take a wide variety of forms depending upon the form of preparation desired for administration, e.g., oral, sublingual, nasal, guttural, rectal, transdermal or parenteral.

In preparing the compositions in oral dosage form, any usual pharmaceutical medium may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, caplets, tablets, microencapsulated granules, microtablets, coated granules and lozenges). Capsules or tablets are a preferred oral dosage form. Controlled release forms may also be used. Because of their ease in administration, lozenges, tablets, pills, caplets, and capsules represent the most advantageous oral dosage unit form, in which case solid pharmaceutical carriers are obviously employed. If desired, tablets may be sugar coated or enteric coated by standard techniques. The compositions of the present invention may be in the form of one or more of these oral dosage forms—i.e., a single dosage may be in multiple forms.

For parenteral products, the carrier will usually comprise sterile water, although other ingredients may be included, e.g., to aid solubility or for preservation purposes. Injectable suspensions may also be prepared, in which case appropriate liquid carriers, suspending agents, and the like may be employed.

Having discussed the composition of the present invention, it will be more clearly perceived and better understood from the following specific examples which are intended to provide examples of the preferred embodiments and do not limit the present invention.

EXAMPLE 1

The composition of the present invention is made in one or more capsules for oral administration in humans and small animals. In a preferred embodiment, each dosage contains:

| Human & Small Animal | Range/Dose |
| --- | --- |
| SAM | 5–5,000 mg |
| Glucosamine | 50–5,000 mg |
| Chondroitin Sulfate | 15–5,000 mg |

EXAMPLE 2

For those situations in which manganese supplementation is desired, a manganese salt is added to the composition of Example 1 so that each dosage contains:

| Human & Small Animal | Range/Dose |
| --- | --- |
| SAM | 5–5,000 mg |
| Glucosamine | 50–5,000 mg |
| Chondroitin Sulfate | 15–5,000 mg |

-continued

| Human & Small Animal | Range/Dose |
|---|---|
| Manganese (as Ascorbate) | 2–75 mg |
| Ascorbate (as Manganese Ascorbate) | 10–500 mg |

EXAMPLE 3

For larger animals, such as horses, the composition of Example 1 is administered as filled scoops.

| Large Animal (Equine) | Range/Dose |
|---|---|
| SAM | 2–20,000 mg |
| Glucosamine | 250–40,000 mg |
| Chondroitin Sulfate | 100–30,000 mg |

EXAMPLE 4

For those situations in which manganese supplementation is desired, manganese salts may be added to the composition of Example 3 so that each dosage contains:

| Large Animal (Equine) | Range/Dose |
|---|---|
| SAM | 2–20,000 mg |
| Glucosamine | 250–40,000 mg |
| Chondroitin Sulfate | 100–30,000 mg |
| Manganese (as Ascorbate) | 10–500 mg |
| Ascorbate (as Manganese Ascorbate) | 50–2,500 mg |

EXAMPLE 5

For a further preferred composition, each dosage contains:

| Human & Small Animal | Range/Dose |
|---|---|
| SAM | 5–5,000 mg |
| Glucosamine | 50–5,000 mg |

EXAMPLE 6

For those situations in which manganese supplementation is desired, a manganese salt is added to the composition of Example 5 so that each dosage contains:

| Human & Small Animal | Range/Dose |
|---|---|
| SAM | 5–5,000 mg |
| Glucosamine | 50–5,000 mg |
| Manganese (as Ascorbate) | 2–75 mg |
| Ascorbate (as Manganese Ascorbate) | 10–500 mg |

EXAMPLE 7

For larger animals, such as horses, the composition of Example 5 is administered as filled scoops.

| Large Animal (Equine) | Range/Dose |
|---|---|
| SAM | 2–20,000 mg |
| Glucosamine | 250–40,000 mg |

EXAMPLE 8

For those situations in which manganese supplementation is desired, manganese salts may be added to the composition of Example 7 so that each dosage contains:

| Large Animal (Equine) | Range/Dose |
|---|---|
| SAM | 2–20,000 mg |
| Glucosamine | 250–40,000 mg |
| Manganese (as Ascorbate) | 10–500 mg |
| Ascorbate (as Manganese Ascorbate) | 50–2,500 mg |

EXAMPLE 9

For a further preferred composition, each dosage contains:

| Human & Small Animal | Range/Dose |
|---|---|
| SAM | 5–5,000 mg |
| Chondroitin Sulfate | 15–5,000 mg |

EXAMPLE 10

For those situations in which manganese supplementation is desired, a manganese salt is added to the composition of Example 9 so that each dosage contains:

| Human & Small Animal | Range/Dose |
|---|---|
| SAM | 5–5,000 mg |
| Chondroitin Sulfate | 15–5,000 mg |
| Manganese (as Ascorbate) | 2–75 mg |
| Ascorbate (as Manganese Ascorbate) | 10–500 mg |

EXAMPLE 11

For larger animals, such as horses, the composition of Example 10 is administered as filled scoops.

| Large Animal (Equine) | Range/Dose |
|---|---|
| SAM | 2–20,000 mg |
| Chondroitin Sulfate | 100–30,000 mg |

EXAMPLE 12

For those situations in which manganese supplementation is desired, manganese salts may be added to the composition of Example 11 so that each dosage contains:

| Large Animal (Equine) | Range/Dose |
| --- | --- |
| SAM | 2–20,000 mg |
| Chondroitin Sulfate | 100–30,000 mg |
| Manganese (as Ascorbate) | 10–500 mg |
| Ascorbate (as Manganese Ascorbate) | 50–2,500 mg |

EXAMPLE 13

For those situations in which methyl donors or methyl donor cofactors are desired, such compounds may be added to the composition of Example 1 so that each dosage contains:

| Human & Small Animal | Range/Dose |
| --- | --- |
| SAM | 5–5,000 mg |
| Glucosamine | 50–5,000 mg |
| Chondroitin Sulfate | 15–5,000 mg |
| vitamin B12 | 0.1–10 mg |

EXAMPLE 14

For those situations in which manganese supplementation is desired, a manganese salt is added to the composition of Example 13 so that each dosage contains:

| Human & Small Animal | Range/Dose |
| --- | --- |
| SAM | 5–5,000 mg |
| Glucosamine | 50–5,000 mg |
| Chondroitin Sulfate | 15–5,000 mg |
| Manganese (as Ascorbate) | 2–75 mg |
| Ascorbate (as Manganese Ascorbate) | 10–500 mg |
| vitamin B12 | 0.1–10 mg |

EXAMPLE 15

For larger animals, such as horses, the composition of Example 13 is administered as filled scoops.

| Large Animal (Equine) | Range/Dose |
| --- | --- |
| SAM | 2–20,000 mg |
| Glucosamine | 250–40,000 mg |
| Chondroitin Sulfate | 100–30,000 mg |
| vitamin B12 | 1–100 mg |

EXAMPLE 16

For those situations in which manganese supplementation is desired, manganese salts may be added to the composition of Example 15 so that each dosage contains:

| Large Animal (Equine) | Range/Dose |
| --- | --- |
| SAM | 2–20,000 mg |
| Glucosamine | 250–40,000 mg |
| Chondroitin Sulfate | 100–30,000 mg |
| Manganese (as Ascorbate) | 10–500 mg |
| Ascorbate (as Manganese Ascorbate) | 50–2,500 mg |
| vitamin B12 | 1–100 mg |

EXAMPLE 17

For a further preferred composition, each dosage contains:

| Human & Small Animal | Range/Dose |
| --- | --- |
| SAM | 5–5,000 mg |
| Glucosamine | 50–5,000 mg |
| vitamin B12 | 0.1–10 mg |

EXAMPLE 18

For those situations in which manganese supplementation is desired, a manganese salt is added to the composition of Example 17 so that each dosage contains:

| Human & Small Animal | Range/Dose |
| --- | --- |
| SAM | 5–5,000 mg |
| Glucosamine | 50–5,000 mg |
| Manganese (as Ascorbate) | 2–75 mg |
| Ascorbate (as Manganese Ascorbate) | 10–500 mg |
| vitamin B12 | 0.1–10 mg |

EXAMPLE 19

For larger animals, such as horses, the composition of Example 17 is administered as filled scoops.

| Large Animal (Equine) | Range/Dose |
| --- | --- |
| SAM | 2–20,000 mg |
| Glucosamine | 250–40,000 mg |
| vitamin B12 | 1–100 mg |

EXAMPLE 20

For those situations in which manganese supplementation is desired, manganese salts may be added to the composition of Example 19 so that each dosage contains:

| Large Animal (Equine) | Range/Dose |
| --- | --- |
| SAM | 2–20,000 mg |
| Glucosamine | 250–40,000 mg |
| Manganese (as Ascorbate) | 10–500 mg |
| Ascorbate (as Manganese | |

-continued

| Large Animal (Equine) | Range/Dose |
| --- | --- |
| Ascorbate) | 50–2,500 mg |
| vitamin B12 | 1–100 mg |

EXAMPLE 21

For a further preferred composition, each dosage contains:

| Large Animal (Equine) | Range/Dose |
| --- | --- |
| SAM | 5–5,000 mg |
| Chondroitin Sulfate | 15–5,000 mg |
| vitamin B12 | 0.1–10 mg |

EXAMPLE 22

For those situations in which manganese supplementation is desired, a manganese salt is added to the composition of Example 21 so that each dosage contains:

| Human & Small Animal | Range/Dose |
| --- | --- |
| SAM | 5–5,000 mg |
| Chondroitin Sulfate | 15–5,000 mg |
| Manganese (as Ascorbate) | 2–75 mg |
| Ascorbate (as Manganese Ascorbate) | 10–500 mg |
| vitamin B12 | 0.1–10 mg |

EXAMPLE 23

For larger animals, such as horses, the composition of Example 21 is administered as filled scoops.

| Large Animal (Equine) | Range/Dose |
| --- | --- |
| SAM | 2–20,000 mg |
| Chondroitin Sulfate | 100–30,000 mg |
| vitamin B12 | 1–100 mg |

EXAMPLE 24

For those situations in which manganese supplementation is desired, manganese salts may be added to the composition of Example 23 so that each dosage contains:

| Large Animal (Equine) | Range/Dose |
| --- | --- |
| SAM | 2–20,000 mg |
| Chondroitin Sulfate | 100–30,000 mg |
| Manganese (as Ascorbate) | 10–500 mg |
| Ascorbate (as Manganese Ascorbate) | 50–2,500 mg |
| vitamin B12 | 1–100 mg |

Many modifications may be made without departing from the basic spirit of the present invention. Accordingly, it will be appreciated by those skilled in the art that within the scope of the appended claims, the invention may be practiced other than has been specifically described herein.

What is claimed is:

1. A composition for treatment and repair and for reducing the inflammation of connective tissue in humans and animals comprising an aminosugar selected from the group consisting of glucosamine, glucosamine salts and mixtures thereof, in combination with S-Adenosylmethionine and a glycosaminoglycan selected from the group consisting of chondroitin, chondroitin salts and mixtures thereof.

2. The composition of claim 1, wherein a dose of the aminosugar ranges from about 50 mg to about 40,000 mg.

3. The composition of claim 2, wherein the dose of the aminosugar for humans and small animals ranges from about 50 mg to about 5,000 mg.

4. The composition of claim 2, wherein the dose of the aminosugar for large animals ranges from about 250 mg to about 40,000 mg.

5. The composition of claim 1, wherein a dose of the glycosaminoglycan ranges from about 15 mg to about 30,000 mg.

6. The composition of claim 5, wherein the dose of glycosaminoglycan for humans and small animals ranges from about 15 mg to about 5,000 mg.

7. The composition of claim 5, wherein the dose of glycosaminoglycan for large animals ranges from about 100 mg to about 30,000 mg.

8. The composition of claim 1, wherein a dose of the S-Adenosylmethionine ranges from about 2 mg to about 20,000 mg.

9. The composition of claim 8, wherein the dose of S-Adenosylmethionine for humans and small animals ranges from about 5 mg to about 5,000 mg.

10. The composition of claim 8, wherein the dose of S-Adenosylmethionine for large animals ranges from about 2 mg to about 20,000 mg.

11. The composition of claim 1, wherein the salt of glucosamine is selected from the group consisting of glucosamine hydrochloride, glucosamine sulfate, and N-acetylglucosamine.

12. A method for the treatment and repair and for reducing the inflammation of connective tissue in humans and animals comprising the step of administering any one of the compositions of claim 1 to claim 11 inclusive, to a human or an animal.

13. A composition for treatment and repair and for reducing the inflammation of connective tissue in humans and animals comprising: an aminosugar selected from the group consisting of glucosamine, glucosamine salts and mixtures thereof, in combination with S-Adenosylmethionine and a glycosaminoglycan selected from the group consisting of chondroitin, chondroitin salts, and mixtures thereof, wherein a dose of the aminosugar ranges from about 50 mg to about 40,000 mg, a dose of the glycosaminoglycan ranges from about 15 mg to about 30,000 mg, and a dose of the S-Adenosylmethionine ranges from about 5 mg to about 40,000 mg.

* * * * *